United States Patent [19]

Yamaguchi

[11] Patent Number: 5,581,191
[45] Date of Patent: Dec. 3, 1996

[54] MICROWAVE DENSITOMETER

[75] Inventor: Seiji Yamaguchi, Sagamihara, Japan

[73] Assignee: Kabushiki Kaisha Toshiba, Kawasaki, Japan

[21] Appl. No.: 524,251

[22] Filed: Sep. 6, 1995

[30] Foreign Application Priority Data

Sep. 12, 1994 [JP] Japan .................................. 6-217251

[51] Int. Cl.$^6$ ............................ G01R 27/04; G01R 27/32
[52] U.S. Cl. ........................ 324/637; 324/639; 324/640; 73/61.44; 73/61.41; 73/861.08
[58] Field of Search .................................... 324/637, 639, 324/640, 642; 73/61.41, 61.43, 61.44, 61.71, 861.04, 861.08

[56] References Cited

U.S. PATENT DOCUMENTS

| | | | |
|---|---|---|---|
| 3,813,924 | 6/1974 | Agar | 73/61.41 |
| 5,001,067 | 3/1991 | Coleman et al. | 73/61.43 |
| 5,006,785 | 4/1991 | Revus | 324/639 |
| 5,101,163 | 3/1992 | Agar | 324/639 |
| 5,313,168 | 5/1994 | Ogawa | 73/61.43 |
| 5,383,353 | 1/1995 | Marrielli et al. | 73/61.43 |
| 5,502,393 | 3/1996 | Yamaguchi et al. | 324/637 |

FOREIGN PATENT DOCUMENTS

| | | |
|---|---|---|
| 59-19846 | 2/1984 | Japan . |
| 2-238348 | 9/1990 | Japan . |

*Primary Examiner*—Maura K. Regan
*Attorney, Agent, or Firm*—Oblon, Spivak, McClelland, Maier & Neustadt, P.C.

[57] ABSTRACT

A microwave densitometer comprises a phase difference detecting section for detecting a phase difference between a microwave generated from a microwave generator and a microwave received by a microwave receiver, a rotation number updating section for varying a value of number of rotations "n", a correcting section for obtaining a difference value $\Delta\Theta$ indicating a difference between a true phase difference $\Theta_2$ and a reference phase difference $\Theta_1'$ a signal converter for converting the difference value $\Delta\Theta$ to a concentration signal an operation mode setter for setting a operation mode, and a holding circuit for holding the number of rotations "n" and the apparent phase difference $\Theta_2'$ when a concentration measuring operation of the fluid to be measured is switched to a non-measuring operation in response to a change of the operation mode set to the operation mode setter.

15 Claims, 8 Drawing Sheets

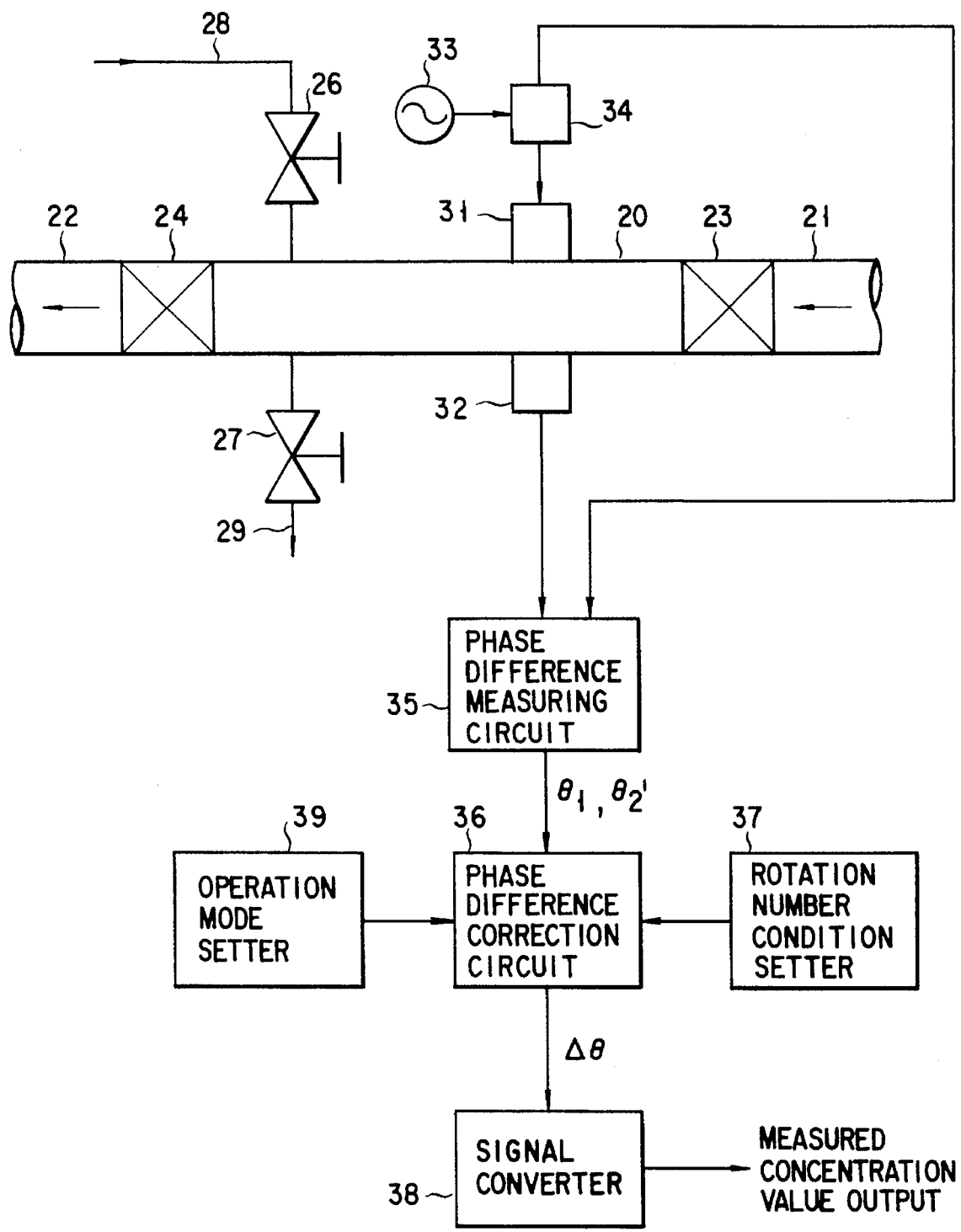
F I G. 1

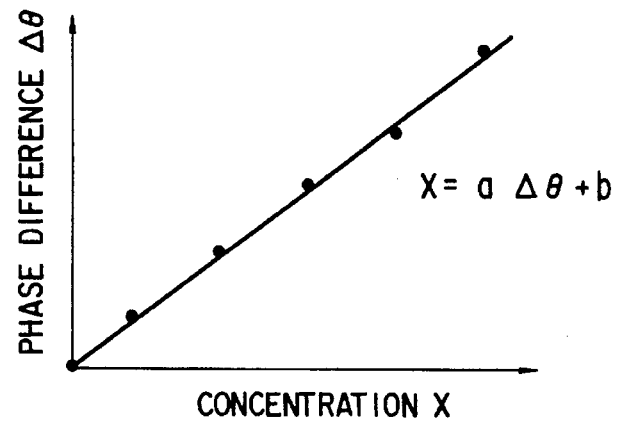
FIG. 8
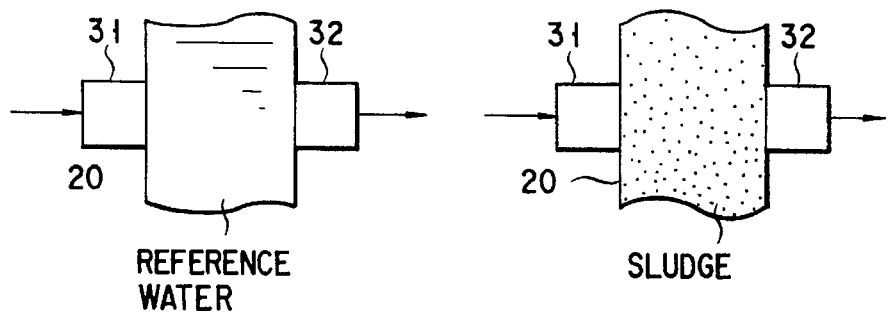
FIG. 9A    FIG. 9B
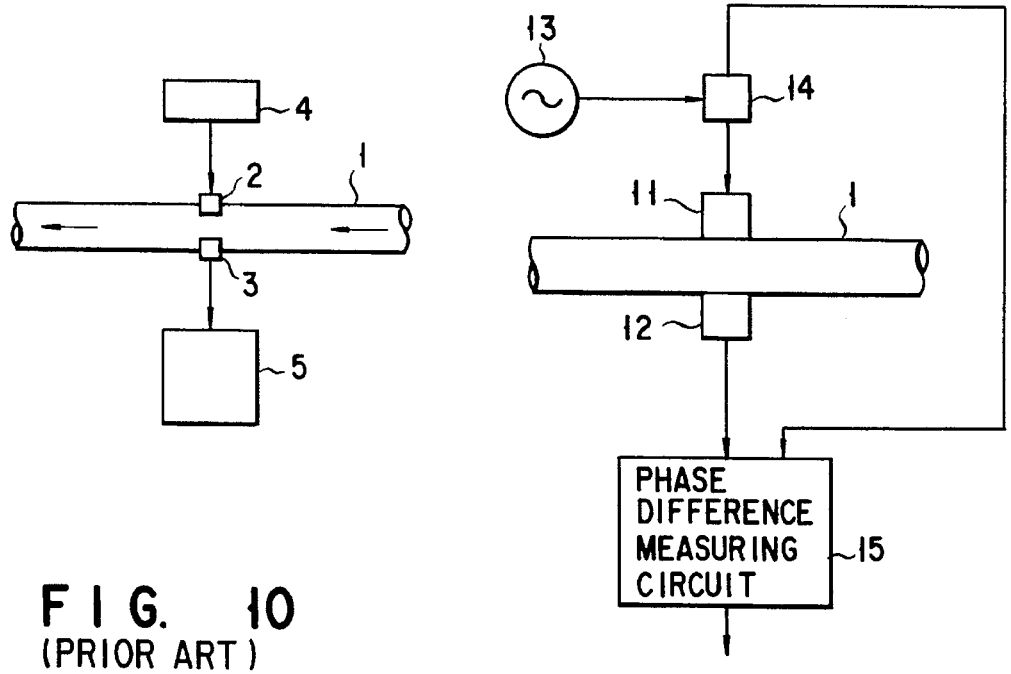
FIG. 10 (PRIOR ART)
FIG. 11 (PRIOR ART)

MICROWAVE DENSITOMETER

BACKGROUND OF THE INVENTION

1. Field of the Invention

The present invention relates to an apparatus for measuring a density of suspension substance (e.g., sludge, pulp, or other various substances) contained in fluid or a concentration of various dissolved substances dissolved in fluid and, more particularly, to a microwave densitometer for reliably measuring a concentration of suspension substance or the like in a wide range of concentration measurement from low to high concentrations.

2. Description of the Related Art

A densitometer for measuring a density of fluid to be measured by using an ultrasonic wave is known. Referring to FIG. 10, a measuring principle of a conventional ultrasonic densitometer will be described. The ultrasonic densitometer is typically so constructed that an ultrasonic transmitter 2 and an ultrasonic receiver 3 are so oppositely located on an interior wall of tube 1, and a fluid to be measured flow in the tube 1 is in contact with the transmitter and the receiver 3. An ultrasonic oscillator 4 is connected to the ultrasonic transmitter 2, and an ultrasonic attenuation factor measuring circuit 5 is connected to the ultrasonic receiver 3.

In this ultrasonic densitometer, an ultrasonic wave radiated from the ultrasonic transmitter 2 to the ultrasonic receiver 3 corresponding to inputting of the ultrasonic signal from the ultrasonic oscillator 4 to the ultrasonic transmitter 2. The ultrasonic wave propagated in the fluid in the tube 1 is received by the ultrasonic receiver 3. An intensity of the ultrasonic wave propagated in the fluid is attenuated in response to a density of suspension substance existing in the fluid.

The ultrasonic receiver 3 converts the ultrasonic wave thus attenuated into an electric signal responsive to its received intensity, and sends the electric signal to the ultrasonic wave attenuation factor measuring circuit 5. A calibration curve for defining the relationship between the density of suspension substance and ultrasonic wave reception intensity is set to the attenuation factor measuring circuit 5. The attenuation factor measuring circuit 5 converts the ultrasonic wave reception intensity into a concentration based on the calibration curve.

However, since the above-described ultrasonic densitometer must bring the transmitter 2 and the receiver 3 into contact with fluid flowing in the tube 1, the suspension substance is feasibly adhered to its contact surface, and hence it is necessary to periodically clean the contact surface. Particularly, when fluid such as sewage sludge flows, possibility of adherence of the suspension substance is enhanced.

Therefore, an ultrasonic densitometer of a structure in which suspension substance is not adhered is considered. This ultrasonic densitometer has an ultrasonic transmitter 2 and an ultrasonic receiver 3 located on exterior wall of the tube 1. However, the ultrasonic densitometer of this type must be reduced in thickness of a tube wall of a portion where the ultrasonic transmitter 2 and the ultrasonic receiver 3 of the tube 1 are mounted, and hence has problems in terms of its intensity and durability. Further, the ultrasonic densitometer possibly causes a measuring error by the influence of a vibration of the tube 1.

The ultrasonic wave has a very large attenuation factor in gas as compared with that in liquid. Thus, when bubbles are mixed in fluid, attenuation of the ultrasonic wave is remarkably increased as compared with that by suspension substance. As a result, there are possibilities that a concentration of the suspension substance cannot be measured and a measured result indicating higher concentration than actual concentration is obtained.

Therefore, an anti-foaming type densitometer of a structure in which bubbles contained in fluid can be removed is considered. This anti-foaming type densitometer inputs fluid to be measured into a pressurized anti-foaming chamber at a predetermined sampling period, removes bubbles by applying a pressure to the fluid to be measured, and then measures a density of the fluid to be measured. However, since the anti-foaming type densitometer has a type for sampling the fluid to be measured at each predetermined sampling period, the anti-foaming type densitometer cannot continuously measure the density of the fluid to be measured. Since the anti-foaming type densitometer needs a mechanically movable mechanism for sampling the fluid to be measured and applying the pressure to the fluid to be measured, the anti-foaming type densitometer has a problem in terms of reliability.

Since the densitometer using ultrasonic wave utilizes dispersing attenuation of an ultrasonic wave by the suspension substance contained in the fluid to be measured, this densitometer cannot measure the concentration of dissolved substance in the fluid.

Recently, a microwave densitometer in which a labor hour for cleaning suspension substance adhered to a tube can be omitted, a concentration of dissolved substance dissolved in fluid to be measured can be measured and yet the concentration can be continuously measured without sampling work in an anti-foaming chamber and which has excellent performance has been developed.

FIG. 11 illustrates a structural example of a densitometer using a microwave.

This microwave densitometer is so constructed that a microwave transmitting antenna 11 and a microwave receiving antenna 12 are disposed oppositely to a tube 1 in which fluid to be measured flows. The microwave densitometer has a first route for introducing a microwave radiated from a microwave oscillator 13 to a phase difference measuring circuit 15 through a power splitter 14, the sending antenna 11, fluid in the tube and the receiving antenna 12, and a second route for introducing the microwave radiated from the microwave oscillator 13 from the power splutter 14 directly to the phase difference measuring circuit 15. The phase difference measuring circuit 15 detects a phase delay of the microwave passed through the first route to the microwave passed through the second route as a phase difference.

In the state that reference fluid (e.g., city water) is filled in a tube, the microwave is generated from the microwave oscillator 13, and a phase delay $\Theta_1$ of the microwave passed through the reference fluid to the microwave received without passing the reference fluid is measured by the phase difference measuring circuit 15.

Then, the microwave is generated from the microwave oscillator 13 in the state that the fluid to be measured is filled in the tube 1, and a phase delay $\Theta_2$ of the microwave propagated through the fluid to be measured in the tube to the microwave received from the microwave oscillator 13 through the power splitter 14 is measured by the phase difference measuring circuit 15. The phase delay $\Theta_2$ obtained by the measurement of this time is compared with the phase delay $\Theta_1$ previously measured, and its phase delay $\Delta\Theta=(\Theta_2-\Theta_1)$ is substituted in a calibration curve graph to specify its concentration.

More specifically, the density or concentration X is calculated by substituting the phase delay $\Delta\Theta$ in the calibration curve graph defined by a formula of the density or concentration $X=a\Delta\Theta+b$. In the formula, "a" signifies for a gradient of the calibration curve, and "b" signifies for an intercept of the calibration curve.

However, since the microwave densitometer detects the phase delay of the microwave varying in response to the concentration state of the fluid to be measured, following problem arises.

FIG. 12 shows a microwave W1 oscillated from the microwave oscillator 13, a microwave W2 having the phase delay $\Theta_1$ received by the microwave receiving antenna 12 through the reference fluid such as city water or the like, and a microwave W3 having the phase delay $\Theta_2$ received by the microwave receiving antenna 12 through the fluid to be measured of a certain density or concentration state.

The phase delay $\Theta_2$ of the microwave W3 is largely varied according to the density or concentration state of the fluid to be measured. In the case where the fluid to be measured has high concentration, the phase delay $\Theta_2$ might become an angle range of first or second rotations exceeding 360°.

For the convenience of description, $0°\leq\Theta_2\leq360°$ is called zero-th rotation; $360°<\Theta_2<720°$, first rotation; $720°<\Theta_2\leq1080°$; second rotation, i.e., $(n-1)\times360°<\Theta_2\leq n\times360°$ is called "(n−1)-th" rotations. It is assumed that $\Theta_1$ is set to zero-th rotation. n=integer of −1, 0 or 1, 2, 3, . . . .

As illustrated in FIG. 13, if the phase delay $\Theta_2$ of the microwave W4 exist in an angle range of the first rotation since the concentration of the fluid to be measured is high, the phase difference measuring circuit 15 calculates "an apparent phase delay $\Theta_2'$" as a measured result. More specifically, the measured result indicating low concentration irrespective of the fact that the fluid to be measured has the high concentration is obtained.

If a diameter of the tube 1 is large, since a propagation route of the microwave is increased in length, the phase delay $\Theta_2$ of the microwave W3 is increased similarly to the case that the fluid to be measured has the high concentration. If the tube 1 has a large diameter and the fluid to be measured has high concentration, the phase delay $\Theta_2$ might become an angle of second rotations $(720°<\Theta_2\leq1808°)$ exceeding 720°.

It is as described above that the phase delay $\Theta_1$ to become a reference is previously measured by using the reference fluid. With the phase delay $\Theta_1$ set as a zero point, the phase delay $\Theta_2$ of the microwave passed through the fluid to be measured is measured. However, as illustrated in FIG. 14, there arises inconvenience that, when the phase delay $\Theta_1$ at a certain time point is a value near 0°, this is measured as zero point data $\Theta_1$ and then city water is so measured as to check zero point, zero point phase delay $\Theta_1$ is drifted to 0° or less due to water temperature change or the like, and then the phase angle is advanced from zero-th rotation to −1-th rotation to apparently become an angle $\Theta_1'$ near 360°, in which the zero point is apparently largely drifted to a positive side.

SUMMARY OF THE INVENTION

An object of the present invention is to provide a microwave densitometer which can accurately measure a density or concentration of fluid to be measured from a low density or concentration to a high density or concentration, accurately measure a density or concentration of fluid to be measured flowing in a large-diameter tube, further prevent number of rotations from unnecessarily varying due to a tube becoming vacant and has extremely high reliability.

According to the present invention, there is provided a microwave densitometer comprising a measuring tube containing fluid to be measured to flow, a microwave generator for generating a microwave, a microwave transmitter provided in the measuring tube for transmitting the microwave supplied from the microwave generator to the fluid to be measured flowing in the measuring tube, a microwave receiver provided oppositely to the microwave transmitter for receiving the microwave transmitted from the microwave transmitter to the measuring tube, a phase difference detecting section for detecting a phase difference between the microwave generated from the microwave generator and the microwave received by the microwave receiver, a rotation number updating circuit for increasing a number of rotations "n" when apparent phase difference varying in an angle range of 360° is returned to a minimum angle exceeding a maximum angle of the angle range and lowering the value of the number of rotations "n" when the phase difference is returned to a maximum angle side below the minimum angle of the angle range, a correcting circuit for obtaining a phase delay $\Delta\Theta$ indicating a difference between a true phase delay $\Theta_2$ corresponding to the concentration of the fluid to be measured and a reference phase delay $\Theta_1$ from the reference phase delay $\Theta_1$ of the phase difference detected by the phase difference detecting section when reference fluid flows in the measuring tube, an apparent phase delay $\Theta_2'$ of the phase difference detected by the phase difference detecting section when the fluid to be measured flows to the measuring tube to measure the concentration of the fluid to be measured and the number of rotations "n" updated by the rotation number updating circuit in response to the apparent phase delay $\Theta_2'$, a signal converter for converting phase difference $\Delta\Theta$ into a concentration signal indicating the concentration of the fluid to be measured, an operation mode setter for setting an operation mode, and a holding circuit for holding number of rotations "n" and the apparent phase delay $\Theta_2'$ when the concentration measuring operation of the fluid to be measured is switched to a non-measuring operation in response to a changer of the drive mode set to the drive mode setter.

According to the microwave densitometer constructed as described above, reference flows to the measuring tube, the phase difference is measured by the phase difference detecting section, and hence the reference phase delay $\Theta_1$ indicating the phase delay of the microwave to the reference fluid is obtained. When the concentration of the fluid to be measured is measured, the fluid to be measured flows to the measuring tube, and the apparent phase delay $\Theta_2'$ of the phase delay of the microwave to the fluid to be measured is measured by the phase difference detecting section. The correcting circuit obtains the phase difference $\Delta\Theta$ indicating the true phase delay $\Theta_2$ and the reference phase delay $\Theta_1$ from the apparent phase delay $\Theta_2'$ and the number of rotations "n" updated by the rotation number updating circuit in response to the apparent phase delay $\Theta_2'$. The phase difference $\Delta\Theta$ is converted to a concentration signal indicating the concentration of the fluid to be measured by the signal converter.

As described above, when this microwave densitometer is switched from the concentration measuring operation of the fluid to be measured to the non-measuring operation, the possibility that the measuring tube temporarily becomes vacant is high. For example, when a zero-point regulation is executed, fluid to be measured in the measuring tube is discharged so that the measuring tube temporarily becomes vacant to introduce reference fluid such as city water into the measuring tube. Or, in the case where sludge stored in a sludge tank is intermittently discharged through the measuring tube, the measuring tube might become, except when the sludge is passed, vacant. When concentration measurement of fluid to be measured is restarted, number of rotations "n" is determined from the apparent phase delay $\Theta_2'$ finally measured and the apparent phase delay $\Theta_2'$ initially measured after the restarting. When the concentration measurement is not executed, if the number of rotations "n" is updated according to the apparent phase difference $\Theta_2'$ of the microwave passed through the vacant measuring tube, the number of rotations "n" might largely change to a value separate from its reality. When the concentration measurement of the fluid to be measured is restarted, if the concentration is measured based on such low reliability apparent phase delay $\Theta_2'$ and the number of rotations "n", the measured value entirely different from the reality might be calculated.

This microwave densitometer can prevent the measured value largely separated from the reality from being measured when the concentration measurement of the fluid to be measured is restarted by holding the number of rotations "n" and the apparent phase delay $\Theta_2'$ at values immediately before the concentration measuring operation is switched to the non-measuring operation.

The microwave densitometer of the present invention determines the value of the number of rotations "n" by comparing the apparent phase delay $\Theta_2'$ held in the holding circuit with the apparent phase delay $\Theta_2'$ measured this time in the case where "a maintenance mode" is returned to "a measuring mode" or "external interlocking mode" is designated and a measuring operation is started.

According to the microwave densitometer, when the "maintenance mode" is returned to the "measuring mode" or when the measuring operation of the "external interlocking mode" is started, the apparent phase delay $\Theta_2'$ held in the holding circuit is compared with the apparent phase delay $\Theta_2'$ measured this time, and the value of the number of rotations "n" is determined based on the compared result.

The microwave densitometer of the present invention comprises a condition setter for setting a high concentration value $X_{max}$ which cannot exist as an object to be measured, and a negative concentration value $X_{min}$ which cannot exist even if the zero point is drifted to compare the measured concentration value measured in a normal concentration measuring state with the high concentration value $X_{max}$ or the negative concentration value $X_{min}$ to obtain valid number of rotations "n", thereby calculating the concentration of the fluid to be measured by using the number of rotations "n".

According to the microwave densitometer, the high concentration value $X_{max}$ which cannot exist as an object to be measured and the negative concentration value $X_{min}$ which cannot exist even if the zero point is drifted are previously set. Then, the concentration calculated value measured in the normal concentration measuring state is compared with the high concentration value $X_{max}$ and the negative concentration value $X_{min}$ to obtain a valid number of rotations "n". The concentration of the fluid to be measured is obtained by using the number of rotations "n".

BRIEF DESCRIPTION OF THE DRAWINGS

FIG. 1 is a structural view of a microwave densitometer according to an embodiment of the present invention;

FIG. 8 is a view showing a calibration curve graph;

FIG. 9A is a view showing the state that reference fluid is filled in a measuring tube;

FIG. 9B is a view showing the state that fluid to be measured is filled in the measuring tube;

FIG. 10 is a principle diagram of an ultrasonic densitometer;

FIG. 11 is a principle diagram of the microwave densitometer;

DETAILED DESCRIPTION OF THE PREFERRED EMBODIMENTS

Figure 2:
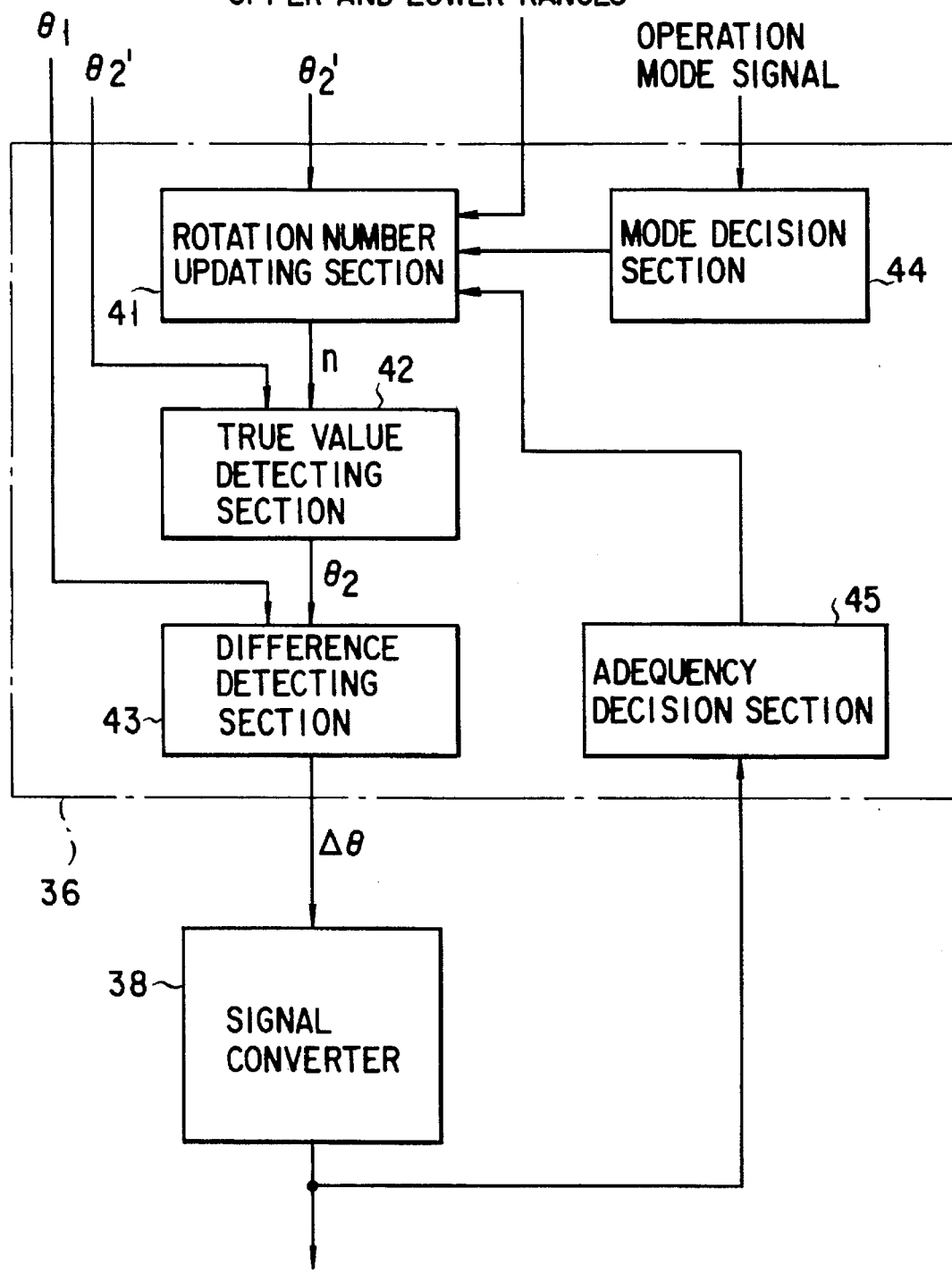
FIG. 2 is a functional block diagram of a phase correcting circuit.

Embodiments of the present invention will be described with reference to the accompanying drawings.

FIG. 1 is a structural view of a microwave densitometer according to an embodiment of the present invention.

This microwave densitometer is so constructed that a measuring tube 20 is disposed between an upstream side tube 21 and a downstream side tube 22 through gate valves 23 and 24. The measuring tube 20 has a water feed valve 26 and a drain valve 27. A water service tube 28 for introducing reference fluid such as city water is connected to the water feed valve 26, and a water distribution tube 29 is connected to the drain valve 27.

The measuring tube 20 is formed at positions opposed through a tube axis with opening windows for introducing and radiating a microwave. An antenna mounting plate is mounted in the opening windows through hermetic seal packings. A transmitting antenna 31 and a receiving antenna 32 are intimately mounted at the antenna mounting plate via insulators. The insulators of the antenna mounting plate are formed of fiber resin plastic (FRP), vinyl chloride resin or other insulator.

A microwave oscillator 33 for generating a microwave is provided in a transmission system of the densitometer, and an output of the microwave oscillator 33 is transmitted to the transmitting antenna 31 through a power splitter 34.

On the other hand, a receiving system of the densitometer has a phase difference measuring circuit 35, a phase difference correcting circuit 36, a rotation number condition setter 37, a signal converter 38 and an operation mode setter 39.

The phase difference measuring circuit 35 receives a microwave transmitted wave from the power splitter 34 as a reference signal together with a received wave of the microwave from the receiving antenna 32, and measures an apparent phase delay of the received wave to the microwave transmitted wave.

The phase difference correcting circuit 36 has a rotation number updating section 41 for determining number of rotations "n", a true value detecting section 42 for obtaining a true phase delay $\Theta_2$ from the number of rotations "n" determined by the rotation number updating section 41, a difference value detecting section 43 for detecting a difference value between the true phase delay $\Theta_2$ and the reference phase delay $\Theta_1$, a mode decision section 44 for deciding a operation mode, and a adequency decision section 45 for judging validity of measured concentration.

The rotation number condition setter 37 manually sets upper and lower ranges of an angle range of 0° to 360°, a high concentration value $X_{max}$ which cannot occur as an object to be measured, a negative concentration value $X_{min}$ which cannot occur even if a zero point is drifted, and an arbitrary number of rotations "n".

The signal converter 38 is set with a calibration curve graph data illustrated in FIG. 8, obtains a concentration value corresponding to a phase difference $\Delta\Theta$ to be input from the phase difference correcting circuit 36 based on the calibration curve graph data, and outputs a current signal corresponding to the concentration value.

The operation mode setter 39 can set three operation modes of "a measuring mode" for measuring normal concentration, "a maintenance mode" for conducting a maintenance operation such as zero point regulation and the like, and "an external interlocking mode" for measuring only when a signal indicating flow of fluid to be measured in a tube is received.

A calculating principle of the true phase delay $\Theta_2$ of the phase difference correcting circuit 36 will be described.

Figure 7:
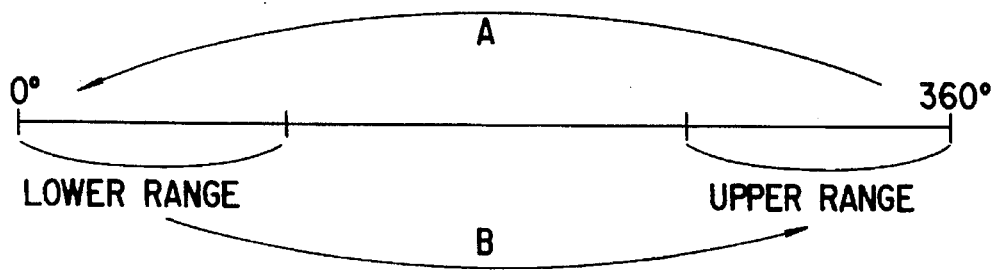
FIG. 7 is a view showing an upper range and a lower range set to an angle range of 0° to 360°.
Figure 12:
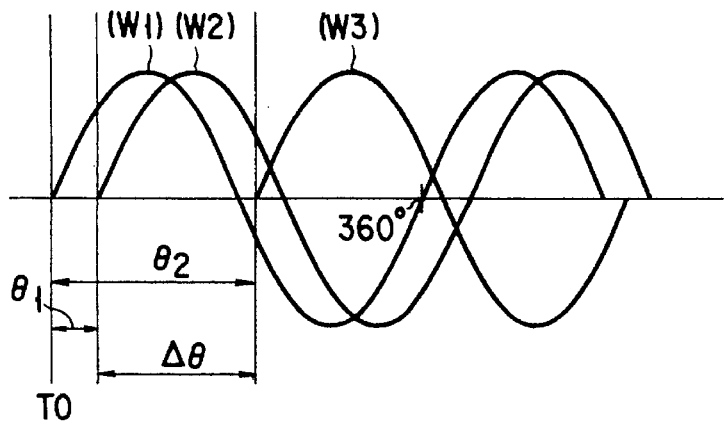
FIG. 12 is a view for explaining a phase delay.
Figure 13:
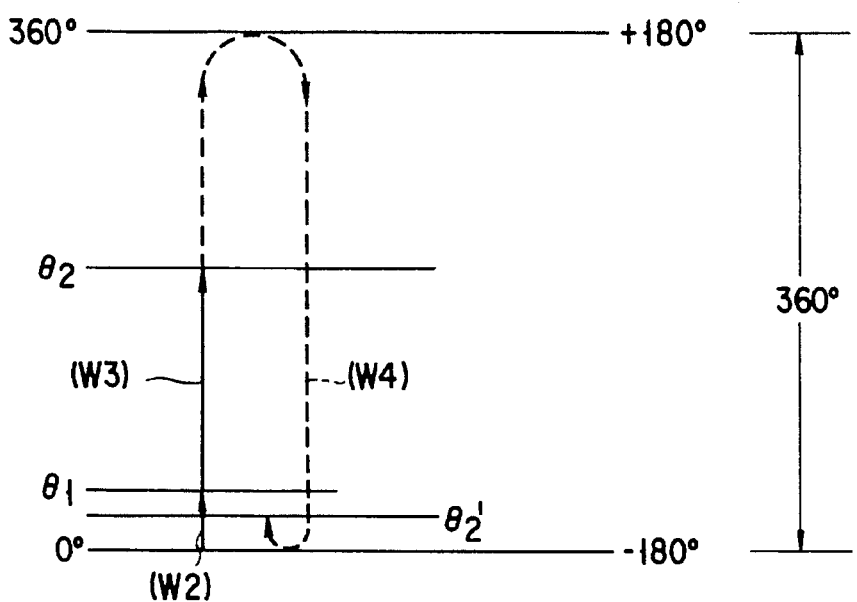
FIG. 13 is a view showing a malfunction of rotation of the phase delay.
Figure 14:
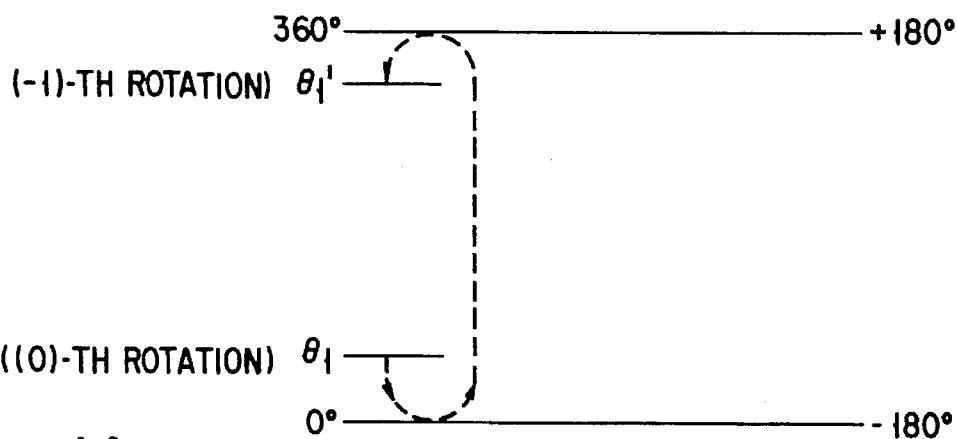
FIG. 14 is a view showing a zero point drift.

As illustrated in FIG. 7, the apparent phase delay $\Theta_2'$ is varied in a range of an angle range of 360°. A predetermined range of the angle range of 0° to 360° from 0° to 360° side is set to a lower range, and a predetermined range of the angle range of 0° to 360° from 360° to 0° side is set to an upper range. For example, a range of 0° to 120° is set as the lower range, and a range of 240° to 360° is set as the upper range.

The apparent phase delay $\Theta_2'$ is measured not continuously but at a time interval of a short time (an interval of 5 sec in this embodiment). If the apparent phase delay $\Theta_2'$ at a certain time point exists in the upper range and the apparent phase delay $\Theta_2'$ at next time point exists in the lower range, number of rotations "n" is updated to n=n+1. If the apparent phase delay $\Theta_2'$ at a certain time point exists in the lower range and the apparent phase delay $\Theta_2'$ at the next time point exists in the upper range, the number of rotations "n" is updated to n=n−1. This number of rotations "n" is used to calculate the true phase delay $\Theta_2$.

The number of rotations "n" based on such a condition is altered on condition that a phenomenon (a concentration change, a temperature change, etc.) in which the apparent phase delay $\Theta_2'$ is largely changed from the upper range to the lower range or vice versa in a range of the same number of rotations "n" (e.g., if number of rotations "n"=0, the true phase delay $\Theta_2'$ changes in a range of 0° to 360°) at a time interval (e.g., 5 sec.) set as a phase delay measuring period does not actually occur. For example, if the apparent phase delay $\Theta_2'$ is changed from the upper range to the lower range or vice versa for 5 sec., change of the number of rotations "n" can be judged.

Then, an operation of the densitometer of this embodiment constructed as described above will be described with reference to FIGS. 3 to 6.

An arbitrary operation mode is previously set from the operation mode setter 39 to the phase difference correcting circuit 36. For example, when maintenance and inspection of the densitometer is executed, the "maintenance mode" is set. In the case where an intermittent operation for draining sludge from the tank to the tube 21 by driving a pump when the sludge stored in the tank reaches a specified water level is executed, the "external interlocking mode" is set.

In this embodiment, the mode decision section 44 decides an operation mode set to the phase difference correcting circuit 36 as the operation is started at a step S1. If the "measuring mode" is set, processes of steps S2 to S9 are executed.

In this case, if the reference phase delay $\Theta_1$ is not held in the difference value detecting section 43 of the phase difference correcting circuit 36, the reference phase delay $\Theta_1$ is previously measured. Upon measuring of the reference phase delay $\Theta_1$, the gate valves 23 and 23 are closed, and the drain valve 27 is then opened to drain fluid to be measured such as sludge is drain. Thereafter, the water feed valve 27 is closed, and city water is fully filled in the tube 20.

As described above, after the city water is fully filled in the tube 20, as illustrated in FIG. 9A, the microwave signal is transmitted from the microwave oscillator 33. This microwave is transmitted from the transmitting antenna 31 through the power splitter 34, and received by the receiving antenna 32 by propagating through the city water in the measuring tube. The received wave is input to the phase difference measuring circuit 35.

A part of the microwave transmitted wave is blanched at the power splitter 34 to the phase difference measuring circuit 35. The phase difference measuring circuit 35 compares the microwave transmitted from the power splitter 34 with the microwave received at the antenna 32 to measure the reference phase delay $\Theta_1$ of the reference fluid. The reference phase delay $\Theta_1$ thus measured is transmitted to the phase difference correcting circuit 36.

The phase difference correcting circuit 36 stores the reference phase delay $\Theta_1$ input from the phase difference measuring circuit 35 in the difference value detecting section 43. The phase difference correcting circuit 36 sets n=0 as an initial value of the number of rotations from the rotation number condition setter 37.

Then, the apparent phase delay $\Theta_2'$ of the fluid to be measured is measured at a step S2. More specifically, the drain valve 27 is opened. Then, after the city water in the measuring tube 20 is drained, the gate valves 23 and 24 are opened, and the fluid to be measured containing substance to be measured flows. The microwave signal is oscillated from the microwave oscillator 33 in this state. This microwave signal is transmitted to the transmitting antenna 31 and the phase difference measuring circuit 35 through the power splitter 34 similarly to the above description.

As illustrated in FIG. 9B, when the microwave transmitted from the transmitting antenna 31 is arrived at the receiving antenna 32 by propagating through the fluid to be measured in the measuring tube 20, the receiving antenna 32 outputs the microwave signal having a phase delay responsive to the density or concentration of the fluid to be measured. The phase difference measuring circuit 35 measured the apparent phase delay $\Theta_2'$ of the microwave signal having the phase delay responsive to the density or concentration of the fluid to be measured. Thus, the microwave is transmitted to the fluid to be measured in the state that the fluid to be measured containing the substance to be measured flows, and the apparent phase delay $\Theta_2'$ is measured in a period of a short time (e.g., each 5 sec.).

Figure 5:
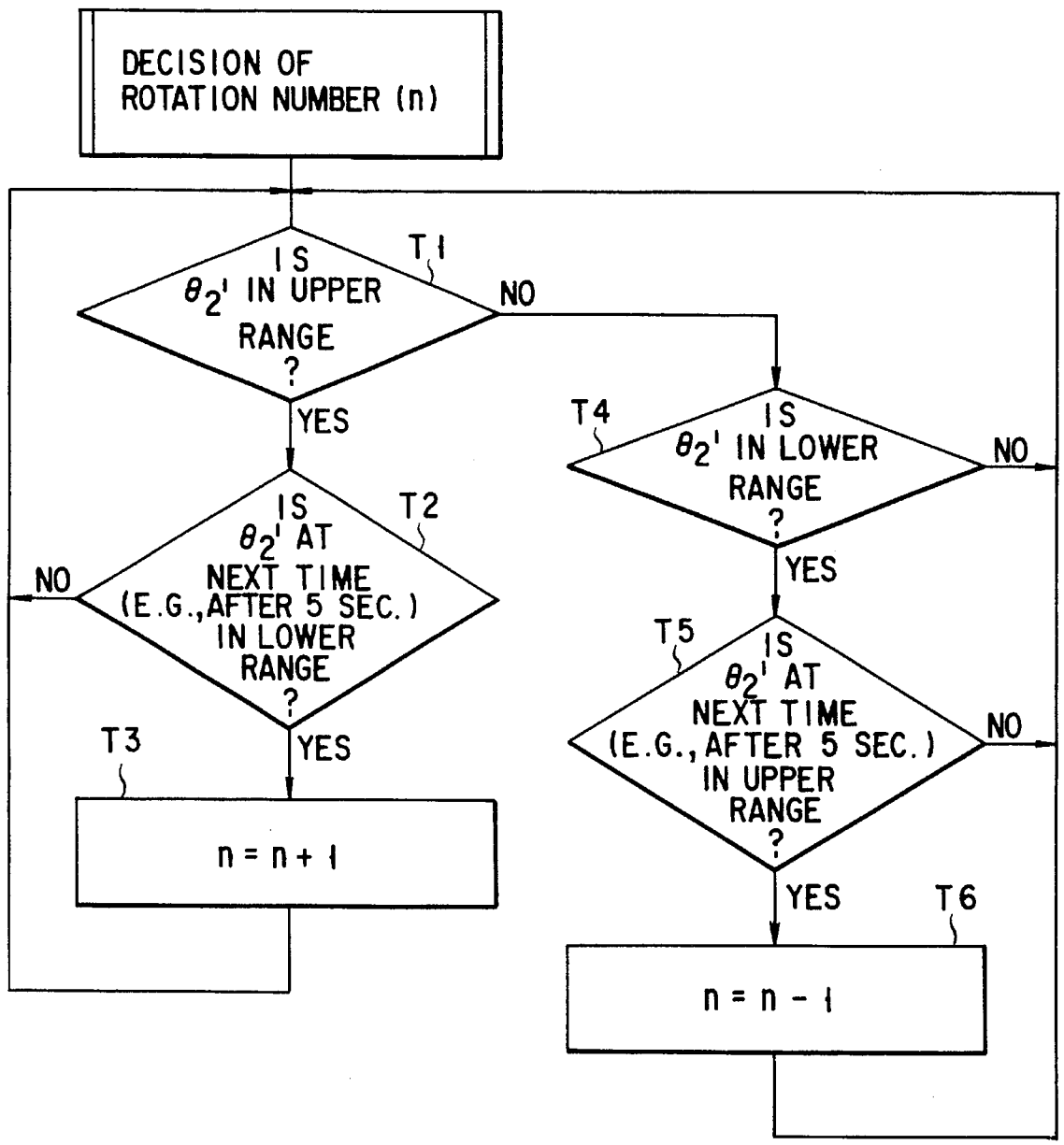
FIG. 5 is a flow chart of rotation number updating operation of the microwave densitometer according to the embodiment.

When the apparent phase delay $\Theta_2'$ is measured, number of rotations "n" is determined based on a flow chart illustrated in FIG. 5 at a step S3. More specifically, the upper and lower ranges for deciding the number of rotations and the initial value n=0 of the number of rotations are read from the rotation, number condition setter 37. The apparent phase delay $\Theta_2'$ is fetched from the phase difference measuring circuit 35, and whether is the apparent phase delay $\Theta_2'$ existed in the upper range or not is judged at a step T1 in FIG. 5. If the apparent phase delay $\Theta_2'$ exists in the upper range, whether is the $\Theta_2'$ after 5 sec. existed in the lower range or not is judged at a step T2. If the $\Theta_2'$ after 5 sec., is excised in the lower range, it means that the apparent phase delay $\Theta_2'$ is changed from the upper range to the lower range during 5 sec. as indicated by change A in FIG. 7, and hence the number of rotations "n" is updated to n=n+1 at a step T3.

If the apparent phase delay $\Theta_2'$ fetched from the phase difference measuring circuit 35 does not belong to the upper range, whether is the $\Theta_2'$ existed in the lower range or not is judged at a step T4. If the $\Theta_2'$ is excited in the lower range, whether is the $\Theta_2'$ measured after 5 sec. is existed in the upper range or not is judged at a step T5. If the $\Theta_2'$ measured after 5 sec. is excised in the upper range, it means that the $\Theta_2'$ is changed from the lower range to the upper range during 5 sec like a change B illustrated in FIG. 7, and hence the number of rotations "n" is updated to n=n-1 at a step T6.

Incidentally, in the other cases, the number of rotations "n" is not changed.

When the number of rotations "n" is determined in the process of the step S3, the true value detecting section 42 calculates the true phase delay $\Theta_2$ based on the following formula (1) at a step S4

$$\Theta_2 = \Theta_2' + n \times 360° \quad (1)$$

Further, the difference value detecting section 43 calculates the phase difference $\Delta\Theta$ based on the following formula (2) at a step S5.

$$\Delta\Theta = \Theta_2 - \Theta_1 \quad (2)$$

The $\Delta\Theta$ obtained as described above is input to the signal converter 38, which calculates the density or concentration X at a step S6.

At this time, if the state that the measuring tube 20 temporarily becomes vacant during the measuring operation in the "measuring mode" or the "external interlocking mode" occurs, there is high possibility that the number of rotations "n" is unnecessarily varied.

Figure 6:
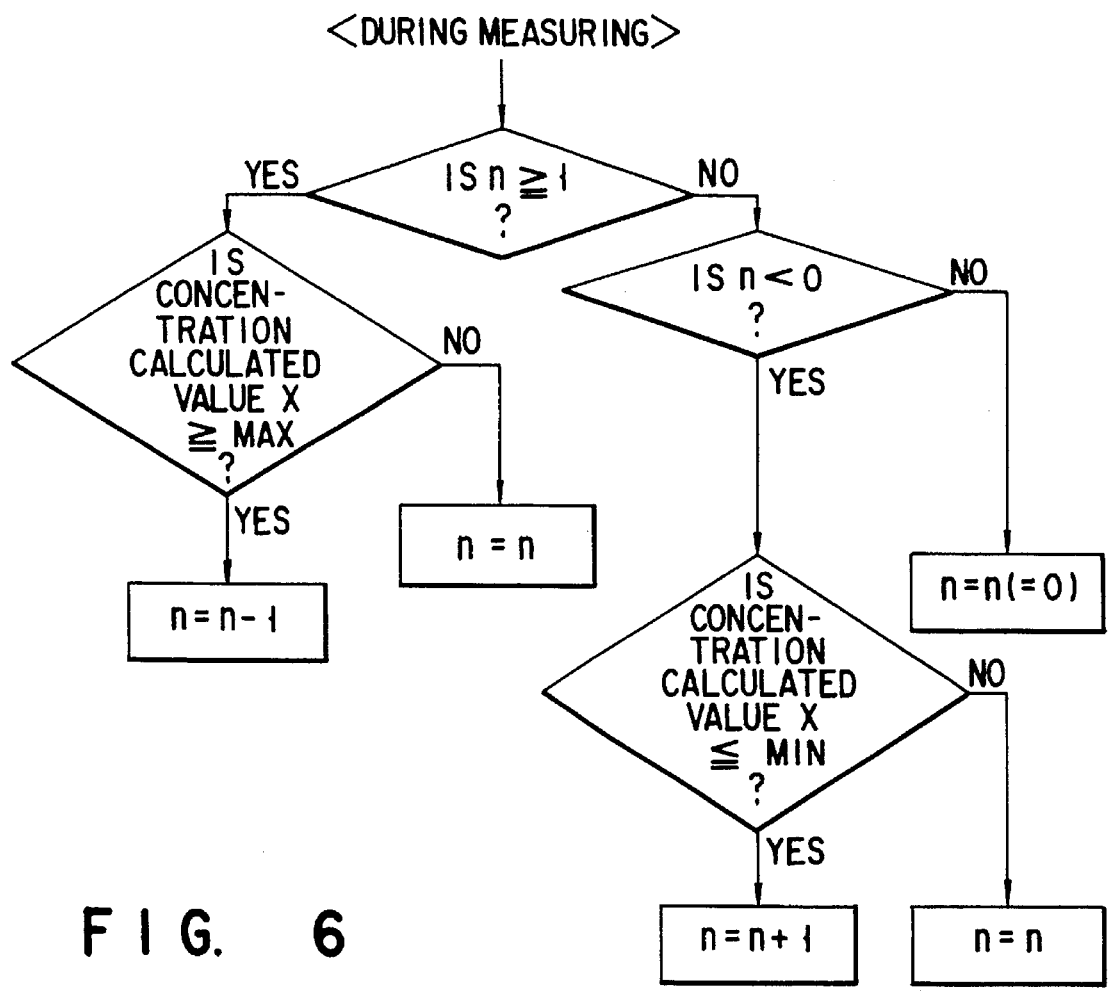
FIG. 6 is a flow chart of judging validity of a concentration of the microwave densitometer according to the embodiment.

Therefore, in the process of the step S7, the adequency decision section 45 judges whether the density or concentration calculated value X is an adequate value or not based on a flow chart of FIG. 6. More specifically, if the number of rotations "n" satisfies the condition of n≧1 and the density or concentration calculated value X satisfies X≧$X_{max}$ the adequency decision section 45 designates the rotation number updating section 41 to update the number of rotations "n" to n=n-1. If the number of rotations "n" satisfies the condition of n<0 and the concentration calculated value X satisfies X≦$X_{min}$ the adequency decision section 45 designates the rotation number updating section 41 to update the number of rotations "n" to n=n+1.

If n≧1 and X<$X_{max}$ are satisfied, the number of rotations "n" is not altered. If n<0 and X>$X_{min}$ are satisfied, the number of rotations "n" is not altered. Further, in the case of n=0, the number of rotations "n" is not altered.

At a step S7, the process is returned to the step S4 as long as the number of rotations "n" is altered, and the concentration X is again calculated by using the number of rotations "n" after the alteration. When the number of rotations "n" is not changed, the density or concentration calculated value X at that time is output as the density or concentration measured value at a step S9. The current signal responsive to the concentration measured value is output. For example, if the concentration measuring range is 0 to 10%, the current signal of 4–20 mA corresponding thereto is output.

On the other hand, in the process of the step S1, the mode except the "measuring mode" is judged, whether the mode is "maintenance mode" or not is further judged. If the "maintenance mode" is judged, the processes of steps S11 to S12 are executed until the "measuring mode" is set. Then, after the "measuring mode" is set, the processes of steps S13 and S14 are executed, and the process is then shifted to the process of the step S2.

In the process of the step S11, the number of rotations "n" output from the rotation number updating section 41 and the apparent phase delay $\Theta_2'$ used in the true value detecting section 42 are held at the values (apparent phase delay $\Theta_2'$ and number of rotations "n") immediately before the non-measuring operation is started. Then, whether the "measuring mode" is set or not is judged in a predetermined period in a step S12.

If the mode decision section 44 detects that the "maintenance mode" is switched to the "measuring mode", the apparent phase delay $\Theta_2'$ is measured similarly to the step S2 in a step S13. A process according to a flow chart of FIG. 5 is executed by using the apparent phase delay $\Theta_2'$ thus measured and the apparent phase delay $\Theta_2'$ held at the step S11 to determined the number of rotations "n" in a step S14. At this time, the $\Theta_2'$ measured in the step S13 is processed as $\Theta_2'$ after 5 sec., in FIG. 5.

If the initial number of rotations "n" is determined immediately after the "maintenance mode" is switched to the "measuring mode", the process is transferred to the step S2 and the density or concentration measurement is executed.

Figure 4:
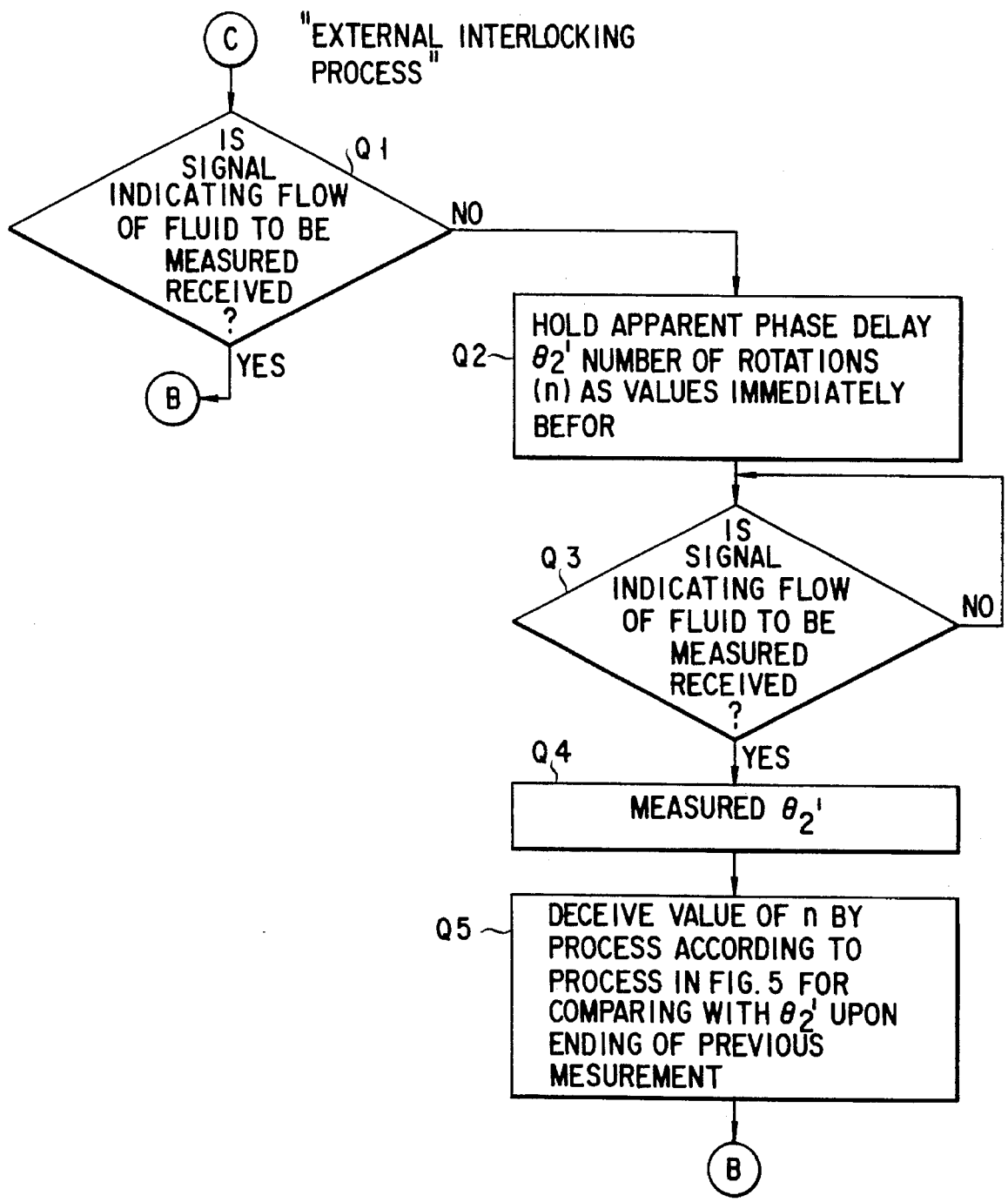
FIG. 4 is a flow chart showing another part of the measuring operation of the microwave densitometer.

If the mode except the "measuring mode" is judged in the process of the step S1 and the mode except the "maintenance mode" is judged in the process of the step S10, an "external interlocking process" illustrated in FIG. 4 is executed. More specifically, whether a signal indicating that fluid to be measured flows is received or not is judged in a step Q1. In the case of this embodiment, whether a pump operation signal of the pump for draining the sludge of the sludge tank to the tube 21 is received or not is judged. The fluid to be measured flows while the pump operation signal is being received.

If the pump operation signal is received in the judgment of the step Q1, the process is transferred to the process of the step S2, and the concentration measuring operation is executed. On the other hand, if the pump operation signal is not received in the judgment of the step Q1, the apparent phase delay $\Theta_2'$ and the number of rotations "n" output from the true value detecting section 43 and the rotation number updating section 41 of the phase difference correcting circuit 36 are held to prevent unnecessary variation of the number of rotations "n" due to the fact that the tube becomes vacant at a step Q2. Thus, if the signal indicating that the fluid to be measured flows in the state that the $\Theta_2'$ and the number of rotations "n" immediately before the non-measuring operation is started, i.e., the pump operation signal is received at the step Q3, the microwave is transmitted to measured the apparent phase delay $\Theta_2'$ at a step Q4. Then, the number of rotations "n" is determined according to the flow chart illustrated in FIG. 5 by using the apparent phase delay $\Theta_2'$ thus measured and the apparent phase delay $\Theta_2'$ held by the process of the step Q2. At this time, the $\Theta_2'$ measured at the step Q4 is processed as the $\Theta_2'$ after 5 sec.

Figure 3:
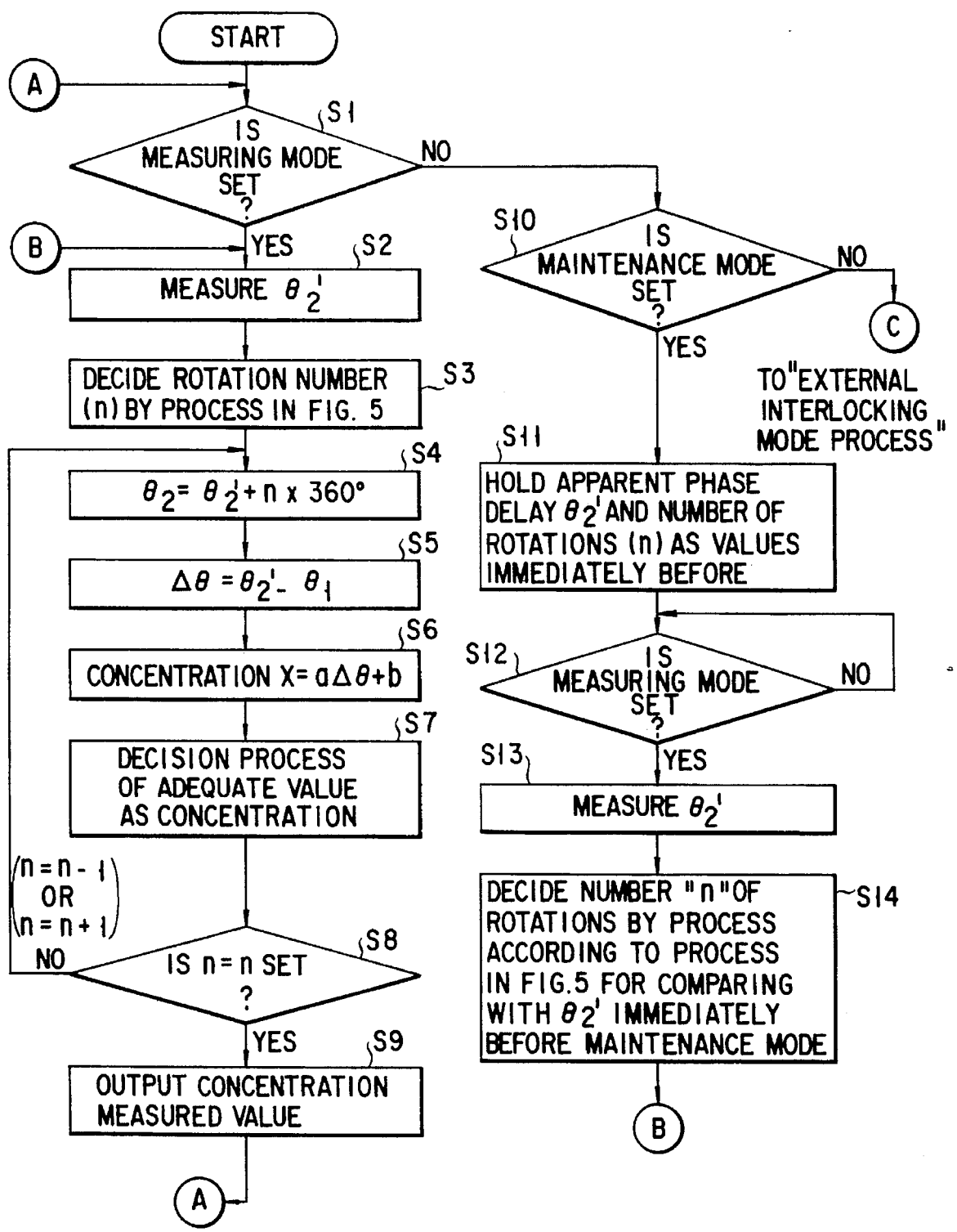
FIG. 3 is a flow chart showing a part of a measuring operation of the microwave densitometer according to the embodiment.

If the number of rotations "n" is determined in the process of the step Q5, the process is transferred to the process of the step S2 illustrated in the flow chart of FIG. 3, and the concentration measurement is executed.

According to the microwave densitometer of this embodiment as described above, the phase delay $\Delta\Theta$ is obtained from the phase delay of the microwave signal obtained by transmitting the microwave from the transmitting side at the time of measuring the reference fluid and the phase delay of the microwave signal obtained under the same measuring conditions at the time of measuring the fluid to be measured, and the concentration of the fluid to be measured is obtained from the phase difference $\Delta\Theta$. Therefore, the concentration can be measured without influence of adherence of the suspension substance contained in the fluid to be measured and bubbles in the fluid to be measured, and the substance dissolved in the fluid to be measured can be measured in its concentration. Further, since the microwave densitometer does not have a mechanical mechanism, long-term high reliability can be maintained.

According to the microwave densitometer of this embodiment, the upper and lower ranges are set to the angle range of 0° to 360°, and the range to which the phase delay $\Theta_2'$ belongs at present is compared with the range in which the phase delay $\Theta_2'$ belongs at the previous time to determined the change of the number of rotations. Therefore, the number of rotations of the apparent phase delay $\Theta_2'$ can be accurately grasped, and the concentration of the fluid to be measured having high concentration can be accurately measured even if the phase delay becomes first rotation or more exceeding 360°, and the concentration can be accurately measured even by a large-diameter concentration detecting tube.

According to the microwave densitometer of this embodiment, the high concentration threshold value $X_{max}$ and the negative concentration threshold value $X_{min}$ are set to the rotation number condition setter 37 and the concentration calculated value X calculated at the number of rotations "n" at the time of measuring the concentration is compared with the high concentration threshold value $X_{max}$ or the negative concentration threshold value $X_{min}$ to determined the optimum number of rotations responsive to the present concentration of the fluid to be measured. Therefore, the accurate number of rotations can be always maintained, and the concentration measured value with high reliability can be obtained.

According to the microwave densitometer of this embodiment, the apparent phase delay $\Theta_2'$ and the number of rotations "n" are held at the values immediately before for a period in which the fluid to be measured does not flow at the time of the "maintenance mode" and the "external interlocking mode" by inputting the operation mode from the operation mode setter 39, the number of rotations is prevented from being unnecessarily varied, and if the fluid to be measured flows, number of rotations "n" is newly determined by using the held $\Theta_2'$ and the number of rotations "n". Therefore, even if an air layer is temporarily formed in the concentration detecting tube at the time of maintenance and inspection or the external interlocking, an abnormal increase or decrease in the phase difference obtained by the measurement can be avoided, thereby preventing the generation of the abnormal measured value.

The present invention is not limited to the particular embodiment described above, but can be also executed by the following modifications:

(a) In the embodiments described above, the concentration of the fluid to be measured is measured in the state that the suspension substance flows. However, the concentration may be measured in the state that the suspension substance is steady. In the embodiments described above, city water is used as the reference fluid. However, fluid which contains substance of certain known concentration may be employed.

In the embodiments described above, the measuring tube 20 is so constructed as to be held between the upstream side tube 21 and the downstream side tube 22. However, when a vessel for inputting fluid is provided at a tube for communicating fluid to be measured, or when a bypass tube is provided, the present invention may be applied to the vessel and the bypass tube.

(b) In the embodiments described above, the measurement of the phase difference has been described by a measuring system of 0° to 360°. However, upper and lower ranges are set to the angle range of, for example, −180° to +180°, and number of rotations may be determined.

(c) In the embodiments described above, the case that n=0 is set at the time of regulating the zero point has been described. However, the present invention is not limited to the particular embodiment. For example, n=1 is set, and a process of $\Theta_2=\Theta_2'+(n-1)\times 360°$ may be executed.

(d) The above-described rotation number updating section updates the number of rotations "n" by setting the upper and lower ranges to the angle range and judging the range to which the apparent phase delay $\Theta_2'$ belongs. However, the present invention is not limited to the particularly embodiment. For example, the apparent phase delay $\Theta_2'$ is continuously fetched from the phase difference measuring circuit at the time of measuring concentration of fluid to be measured, the apparent phase delay $\Theta_2'$ is differentiated to detect an increasing or decreasing trend of the $\Theta_2'$. If the apparent phase delay $\Theta_2'$ is passed through the maximum value of the angle range of 360° while increasing, the number of rotations "n" is increased by "1". If the apparent phase delay $\Theta_2'$ is passed through the minimum value of the angle range of 360° while decreasing, the number of rotations "n" is decreased by "1".

Additional advantages and modifications will readily occur to those skilled in the art. Therefore, the invention in its broader aspects is not limited to the specific details, and representative devices shown and described herein. Accordingly, various modifications may be made without departing from the spirit or scope of the general inventive concept as defined by the appended claims and their equivalents.

What is claimed is:

1. A microwave densitometer for measuring a density or concentration of fluid to be measured based on a phase delay of a microwave passed through the fluid to be measured comprising:

a measuring tube for flowing the fluid to be measured;

a microwave generator for generating a microwave;

a microwave transmitter provided in the measuring tube for transmitting the microwave supplied from said microwave generator to the fluid to be measured flowing in said measuring tube, a microwave receiver provided in said measuring tube opposite to said microwave transmitter for receiving the microwave transmitted from said microwave transmitter through the fluid to be measured, phase difference detecting means for detecting an apparent phase difference between the microwave generated by said microwave generator and the microwave received by said microwave receiver, rotation number updating means for increasing a number of rotations "n" when the apparent phase difference varying in an angle range of 360° is shifted to a minimum angle side of the angle range exceeding a maximum angle of the angle range and decreasing the number of rotations "n" when the apparent phase difference is shifted to a maximum angle below the minimum angle of the angle range, correcting means for correcting an apparent phase difference $\Theta_2'$ which detected by said phase difference detecting means when said fluid to be measured flows to said measuring tube, and obtaining a difference value $\Delta\Theta$ indicating a difference between a true phase difference $\Theta_2$ corresponding to a density or concentration of said fluid to be measured and a reference phase difference $\Theta_1$ according to the reference phase difference $\Theta_1$ detected by said phase difference detecting means when the reference fluid flows in said measuring tube, the apparent phase difference $\Theta_2'$ and the number of rotations "n" updated by said rotation number updating means in response to the apparent phase difference $\Theta_2'$, signal converting means for converting the difference value $\Delta\Theta$ into a concentration signal indicating the density or concentration of said fluid to be measured;

operation mode setting means for setting an operation mode; and holding means for holding the number of rotations "n" and the apparent phase difference $\Theta_2'$ when a concentration measuring operation of said fluid to be measured is switched to a non-measuring operation in response to a change of the operation mode set in said operation mode setting means.

2. A densitometer according to claim 1, wherein said operation mode setting means selectively sets two or more operation modes including "a measuring mode" for normally measuring and "a maintenance mode" for stopping fluid to be measured flowing in said measuring tube for maintenance, and said holding means holds said number of rotations "n" and said apparent phase difference $\Theta_2'$ at that time when said operation mode setting means is set with said "maintenance mode".

3. A densitometer according to claim 2, wherein said rotation number updating means determines a new number of rotations "n" according to the number of rotations and the apparent phase difference $\Theta_2'$ held by said holding means and an apparent phase difference $\Theta_2'$ measured initially by said phase difference detecting means after the "maintenance mode" is switched to the "measuring mode" when said operation mode is switched from the "maintenance mode" to the "measuring mode".

4. A densitometer according to claim 1, wherein said operation mode setting means is set with two or more modes including the "measuring mode" for normally measuring and the "external interlocking mode" for measuring only while the fluid to be measured flows in said measuring tube, and said holding means holds said number of rotations "n" and said apparent phase difference $\Theta_2'$ at that time when "external interlocking mode" is designated to said operation mode setting means and the density or concentration measurement is stopped.

5. A densitometer according to claim 4, wherein said rotation number updating means determines a new number of rotations "n" according to the number of rotations and said apparent phase difference $\Theta_2'$ held by said holding means and an apparent phase difference $\Theta_2'$ measured initially by said phase difference detecting means after the concentration measurement is restarted when said "external interlocking mode" is designated for said operation mode setting means.

6. A densitometer according to claim 1, wherein said operation mode setting means is set with three or more modes including the "measuring mode" for normally measuring, the "maintenance mode" for stopping the fluid to be measured flowing in said measuring tube for maintenance and the "external interlocking mode" for measuring only while the fluid to be measured flows in said measuring tube, and said holding means holds said number of rotations "n" and said apparent phase delay $\Theta_2'$ at that time when said "maintenance mode" is designated or said "external interlocking mode" is designated and the concentration measurement is stopped.

7. A densitometer according to claim 6, wherein said rotation number updating means determines a new number of rotations "n" from said number of rotations and said apparent phase difference held by said holding means and an apparent phase difference $\Theta_2'$ measured initially by said phase difference detecting means after the "maintenance mode" is switched to the "measuring mode" when said operation mode is switched from the "maintenance mode" to the "measuring mode" and determines a new number of rotations "n" from the number of rotations and said apparent phase difference held by said holding means and the apparent phase difference $\Theta_2'$ measured initially by said phase difference detecting means after the concentration measurement is restarted when said "external interlocking mode" is designated and the concentration measurement is restarted.

8. A densitometer according to claim 1, further comprising:

condition setting means for setting a high concentration value $X_{max}$ which cannot exists in said fluid to be measured and a low concentration value $X_{min}$ which cannot exist as a zero point drift; and adequate judging means for comparing the concentration value measured in a normal concentration measuring state with said high concentration value $X_{max}$ or said low concentration value $X_{min}$ to designate alteration of number of rotations for said rotation number updating means when said concentration value is not adequate.

9. A densitometer according to claim 8, wherein said adequate judging means designates a decrease in number of rotations for said rotation number updating means when said concentration value is larger than said high concentration value $X_{max}$ and designates an increase in number of rotations for said rotation number updating means when said concentration value is smaller than said low concentration value $X_{min}$.

10. A densitometer according to claim 1, wherein said correcting means comprises:

true value detecting means for obtaining a true phase difference $\Theta_2$ from said apparent phase difference $\Theta_2'$ and said number of rotations "n" by the following formula:

$$\Theta_2=\Theta_2'+n\times360°$$

and, difference value detecting means for obtaining said difference value $\Delta\Theta$ from said reference phase difference $\Theta_1$ and said true phase difference $\Theta_2$ by the following formula $$\Delta\Theta = \Theta_2 + \Theta_1.$$

11. A densitometer according to claim 1, wherein said rotation number updating means is set at a predetermined range from a minimum angle to a maximum angle of said angle range as a lower range, set at a predetermined rage from a maximum angle to a minimum angle of said angle range as an upper range and fetched with said apparent phase difference $\Theta_2'$ from said phase difference detecting means at a predetermined time interval for comparing a range to which said apparent phase difference $\Theta_2'$ at a certain time point belongs with a range to which said apparent phase difference $\Theta_2'$ belongs at next time point to update said number of rotations "n".

12. A densitometer according to claim 11, wherein said rotation number updating means decreases only "1" from said number of rotations "n" when said apparent phase difference $\Theta_2'$ at a certain time point belongs to said lower range and said apparent phase difference $\Theta_2'$ at next time belongs to said upper range and increases "1" to said number of rotations "n" when the apparent phase difference $\Theta_2'$ at a certain time point belongs to said upper range and said apparent phase difference $\Theta_2'$ at the next time point belongs to said lower range.

13. A densitometer according to claim 1, wherein said rotation number updating means comprising:

trend detecting means for continuously detecting an increasing or decreasing trend of said apparent phase difference $\Theta_2'$ by fetching said apparent phase difference $\Theta_2'$ from said phase difference detecting means, and said rotation number updating means increases a value of the number of rotations "n" when said apparent phase difference $\Theta_2'$ exceeds the maximum angle of said angle range when said trend detecting means detects an increase of said apparent phase difference $\Theta_2'$, and decreases the value of the number of rotations "n" when said apparent phase difference $\Theta_2'$ exceeds the minimum angle of said angle range when said trend detecting means detects a decrease of said apparent phase difference $\Theta_2$.

14. A densitometer according to claim 1, wherein said rotation number updating means decreases only "1" from said number of rotations "n" when a predetermined range from the minimum angle to the maximum angle of said angle range is set as a lower range, a predetermined range from the maximum angle to the minimum angle for said angle range is set as an upper range, said apparent phase difference $\Theta_2'$ from phase difference detecting means is fetched at a predetermined time interval, said phase difference difference $\Theta_2'$ belongs to said lower range at a certain time and said apparent phase difference $\Theta_2'$ belongs to said upper range at next time point, and increases only "1" to said number of rotations "n" when said apparent phase difference $\Theta_2'$ at the certain time point belongs to said upper range, and said apparent phase difference $\Theta_2'$ at the next time point belongs to said lower range, and said correcting means comprises:

true value detecting means for obtaining from said apparent phase difference $\Theta_2'$ and said number of rotations "n" by following formula:

$$\Theta_2 = \Theta_2' + n \times 360°$$

difference value detecting means for obtaining said difference value $\Delta\Theta$ from said reference phase difference $\Theta_1$ and said true phase difference $\Theta_2$ by following formula:

$$\Delta\Theta = \Theta_2 - \Theta_1$$

said operation mode setting means selectively sets three or more operation modes including "measuring mode" for normally measuring, "maintenance mode" for stopping fluid to be measured flowing in said measuring tub for maintenance and "external interlocking mode" for measuring only while said fluid to be measured flows in said measuring tube, said holding means holds said number of rotations "n" and said apparent phase difference $\Theta_2'$ at that time when said "maintenance mode" is designated or when said "external interlocking mode" is designated and said concentration measurement is stopped, and further said rotation number updating means determines a new number of rotations "n" from said number of rotations and said apparent phase difference held by said holding means and an apparent phase difference $\Theta_2'$ measured initially by said phase difference detecting means after the "maintenance mode" is switched to the "measuring mode" when said operation mode is switched from the "maintenance mode" to the "measuring mode" and determines a new number of rotations "n" from the number of rotations and said apparent phase difference held by said holding means and the apparent phase difference $\Theta_2'$ measured initially by said phase difference detecting means after the concentration measurement is restarted when said "external interlocking mode" is designated and the concentration measurement is restarted.

15. A densitometer according to claim 14, further comprising:

condition setting means for setting a high concentration value $X_{max}$ which cannot exists in said fluid to be measured and a low concentration value $X_{min}$ which cannot exist as a zero point drift; and adequate judging means for comparing the concentration value measured in a normal concentration measuring state with said high concentration value $X_{max}$ or said low concentration value $X_{min}$ to designate alteration of number of rotations for said rotation number updating means when said concentration value is not valid.

* * * * *